United States Patent
Herbst et al.

(10) Patent No.: US 10,593,427 B2
(45) Date of Patent: *Mar. 17, 2020

(54) MOBILE DISCRETE DATA DOCUMENTATION

(71) Applicant: CERNER INNOVATION, INC., Kansas City, KS (US)

(72) Inventors: Damon Matthew Herbst, Shawnee, KS (US); Randolph S. Lantz, Parkville, MO (US); Greg T. Meyer, Smithville, MO (US); Matthew P. Bailey, Liberty, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 110 days.

This patent is subject to a terminal disclaimer.

(21) Appl. No.: 15/918,711

(22) Filed: Mar. 12, 2018

(65) Prior Publication Data
US 2018/0204641 A1    Jul. 19, 2018

Related U.S. Application Data

(63) Continuation-in-part of application No. 14/262,110, filed on Apr. 25, 2014, now abandoned, which is a
(Continued)

(51) Int. Cl.
*G16H 40/60* (2018.01)
*G16H 40/63* (2018.01)
(Continued)

(52) U.S. Cl.
CPC .............. *G16H 40/63* (2018.01); *G06Q 10/10* (2013.01); *G06Q 50/22* (2013.01); *G16H 10/60* (2018.01); *G16H 40/67* (2018.01)

(58) Field of Classification Search
CPC ....................................................... G16H 40/67
(Continued)

(56) References Cited

U.S. PATENT DOCUMENTS

| 4,857,716 A | 8/1989 | Gombrich et al. |
| 5,474,090 A | 12/1995 | Begun et al. |

(Continued)

FOREIGN PATENT DOCUMENTS

| EP | 1786350 B1 | 10/2009 |
| WO | 199859487 A1 | 12/1998 |

(Continued)

OTHER PUBLICATIONS

Preinterview First Office Action received for U.S. Appl. No. 15/246,971, dated Jun. 5, 2019, 6 pages.
(Continued)

*Primary Examiner* — John A Pauls
(74) *Attorney, Agent, or Firm* — Shook, Hardy & Bacon L.L.P.

(57) ABSTRACT

A medical device for facilitating data direction to storage in a patient-specific electronic record is provided herein. In embodiments, the medical device visually presents patient data received from devices that more directly capture physiological data. The medical device is associated with a patient corresponding to the physiological data, and communicates the patient data to a centralized server for processing and forwarding to a database, which includes an electronic record that is specific to the patient. Then, the medical device may be dissociated from the patient.

20 Claims, 14 Drawing Sheets

Related U.S. Application Data continuation of application No. 12/351,601, filed on Jan. 9, 2009, now Pat. No. 8,731,957.

(51) Int. Cl.
  *G06Q 10/10* (2012.01)
  *G06Q 50/22* (2018.01)
  *G16H 10/60* (2018.01)
  *G16H 40/67* (2018.01)

(58) Field of Classification Search
  USPC ............ 726/11; 710/63, 315; 600/300; 370/310; 707/503; 705/3; 701/24; 128/903; 709/250
  See application file for complete search history.

(56) References Cited

U.S. PATENT DOCUMENTS

| | | |
|---|---|---|
| 5,935,224 A | 8/1999 | Svancarek et al. |
| 6,346,886 B1 | 2/2002 | De La Huerga |
| 6,406,426 B1 | 6/2002 | Reuss et al. |
| 6,416,426 B1 | 7/2002 | Nakamura et al. |
| 6,434,644 B1 | 8/2002 | Young et al. |
| 6,760,804 B1 | 7/2004 | Hunt et al. |
| 6,839,753 B2 | 1/2005 | Biondi et al. |
| 6,942,616 B2 | 9/2005 | Kerr, II |
| 7,103,578 B2 | 9/2006 | Beck et al. |
| 8,082,160 B2 | 12/2011 | Collins, Jr. et al. |
| 2002/0002326 A1 | 1/2002 | Causey, III et al. |
| 2002/0116509 A1 | 8/2002 | DeLaHuerga |
| 2002/0120676 A1 | 8/2002 | Biondi et al. |
| 2002/0165875 A1 | 11/2002 | Verta |
| 2003/0016122 A1 | 1/2003 | Petrick |
| 2003/0046109 A1 | 3/2003 | Uchikubo |
| 2003/0087712 A1 | 5/2003 | Nickerson |
| 2004/0010425 A1 | 1/2004 | Wilkes et al. |
| 2004/0133704 A1 | 7/2004 | Krzyzanowski et al. |
| 2005/0108057 A1 | 5/2005 | Cohen et al. |
| 2005/0209886 A1 | 9/2005 | Corkern |
| 2005/0216313 A1 | 9/2005 | Claud et al. |
| 2006/0149590 A1 | 7/2006 | Palmer et al. |
| 2006/0242293 A1 | 10/2006 | Russ |
| 2007/0192133 A1 | 8/2007 | Morgan |
| 2007/0223408 A1 | 9/2007 | Thielke et al. |
| 2007/0255884 A1 | 11/2007 | Kinstler |
| 2008/0040788 A1 | 2/2008 | Steinkogler et al. |
| 2009/0112630 A1 | 4/2009 | Collins et al. |
| 2010/0010320 A1 | 1/2010 | Perkins et al. |
| 2010/0169120 A1 | 7/2010 | Herbst et al. |
| 2010/0287006 A1 | 11/2010 | Cannon et al. |
| 2010/0332257 A1 | 12/2010 | Sims et al. |
| 2011/0010193 A1 | 1/2011 | Zheng et al. |
| 2014/0171753 A1 | 6/2014 | Montejo et al. |
| 2014/0195446 A1 | 7/2014 | Yurach et al. |
| 2015/0182696 A1 | 7/2015 | Kelly et al. |

FOREIGN PATENT DOCUMENTS

| | | |
|---|---|---|
| WO | 199967732 A1 | 12/1999 |
| WO | 2006035351 A2 | 4/2006 |

OTHER PUBLICATIONS

Moorman, Bridget, Biomedical Device Interfacing to Clinical Information Systems: A Primer, Biomedical Instrumentation & Technology, IT World, pp. 205-208. Available at: https://rdcms-aami.s3.amazonaws.com/files/production/public/FileDownloads/BIT/2008_BIT_MJ_Medical_Device_Interfacing.pdf.

Ganous et al., "A Pervasive Computing System for the Operating Room of the Future", University of Maryland Medical School, 2007, 18 pages.

Final Office Action dated Dec. 15, 2017 in U.S. Appl. No. 14/262,110, 13 pages.

Final Office Action dated Sep. 29, 2011 in U.S. Appl. No. 12/351,601, 18 pages.

Non-Final Office Action dated May 10, 2011 in U.S. Appl. No. 12/351,601, 16 pages.

Final Office Action dated Jul. 31, 2012 in U.S. Appl. No. 12/351,601, 24 pages.

Non-Final Office Action dated Feb. 28, 2012 in U.S. Appl. No. 12/351,601,23 pages.

Notice of Allowance dated Jan. 9, 2014 in U.S. Appl. No. 12/351,601, 9 pages.

Final Office Action dated Nov. 21, 2016 in U.S. Appl. No. 14/262,110, 33 pages.

| | |
|---|---|
| PATIENT TO DEVICE ASSOCIATION | |
| TASKS | |
| TAYLOR, HALSEY (MALE) | SEARCH — 811 |
| DOB: 04/01/1970 | |
| FIN: 130920001   MRN: 513906204   PID: 4159928 | |

SICU05

| | | |
|---|---|---|
| DIASTOLIC BLOOD PRESSURE | 80 | MM/HG |
| BP TAKEN | ▸ | — 816 |
| SYSTOLIC BLOOD PRESSURE | 120 | MM/HG — 818 |
| BP TAKEN | ▸ | |
| HEART RATE | 60 | BPM |
| TEMPERATURE | 37 | DEG C |
| TEMPERATURE LOCATION | ORAL ▸ | |
| PULSE RATE FROM PLETHYSMOGRAM | 60 | BPM |
| RESPIRATORY RATE | | BR/MIN |
| PAIN SCALE | ▸ | |

ACQUIRED FROM DEVICE: 10/27/08 11:17:32 AM

REACQUIRE DATA     CANCEL     SIGN

| | | 2:25 PM | 2:27 PM | 2:32 PM |
|---|---|---|---|---|
| VITALS INET | | | 9/4/2008 | |
| ORAL TEMP | DEGC | | | |
| TYMPANIC TEMP | DEGF | | | |
| RECTAL TEMP | DEGF | | | |
| AXILLARY TEMP | | | | |
| CORE TEMP | DEGC | 37 DEGC | 37 DEGC → | 37 DEGC → |
| HEART RATE | BPM | 60 | 60 → | 60 → |
| PULSE RATE | BPM | 60 | 60 → | 60 → |
| FETAL HEART TONES | | | | |
| O2 SAT | % | | | |
| O2 MODE | | | | |
| OXYGEN AMOUNT | -/- | | | |
| BLOOD PRESSURE | | 120 MMHG/80 MMHG | 120 MMHG/80 MMHG | 120 MMHG/80 MMHG |
| MEAN BP | | 90 MMHG | 90 MMHG | 90 MMHG |

FIG. 11.

| PATIENT TO DEVICE ASSOCIATION | | | |
|---|---|---|---|
| TASKS | | | |
| LAST NAME: TAYLOR | | | |
| FIRST NAME: | | | |
| ID: MRN ▾ | | | |
| NAME | GENDER | DATE OF BIRTH | |
| TAYLOR, BRANDON | | | |
| TAYLOR, CAROL | F | 03/08/1995 | |
| TAYLOR, HALSEY | M | 04/01/1970 | |
| TAYLOR, TYRONNE | | | |
| TAYLOR, VERN | M | 04/05/1960 | |

SEARCH  CANCEL

1110 — (last name/first name/ID fields)
1112 — (name list)
1114 — SEARCH
1100

FIG. 13.

MOBILE DISCRETE DATA DOCUMENTATION

CROSS REFERENCE TO RELATED APPLICATIONS

This nonprovisional patent application, entitled "Mobile Discrete Data Documentation," is a continuation-in-part of co-pending U.S. patent application Ser. No. 14/262,110, filed on Apr. 25, 2014 and entitled "Mobile Discrete Data Documentation," which is a continuation of U.S. Pat. No. 8,731,957, having issued on May 20, 2014 and entitled "Mobile Discrete Data Documentation," and this nonprovisional patent application is also related to the subject matter of co-pending U.S. patent application Ser. No. 15/246,971, filed on Aug. 25, 2016 and entitled "Mobile Discrete Data Documentation." The entirety of each of the aforementioned applications is incorporated by reference herein.

BACKGROUND

Prior systems lacked the ability to efficiently and effectively record verified data from a medical device safely into a patient's EMR. Prior systems could not record accurate and timely data from a medical device the proper patient's record, as further enriched with a clinician's observations. These problems arose from a computer network environment in which mobile medical devices are meant to intelligently interface with multiple patients and respective electronic patient records through a computer network architecture. These technological difficulties arose from the use of specialized computer network architectures and technical implementations in which medical device computers communicate on a computer network.

Additionally, transmitting patient information, such as data from a medical device to a patient's electronic medical record (EMR), has been a difficult, error-prone, and time-consuming process for the user, such as a clinician, who is responsible for taking the vitals from the patient and transferring the data to the patient's EMR. For example, when a patient's vitals are taken, such as temperature, blood pressure, heart rate, etc., a clinician may use a medical device to take the vitals and write down the data on a piece of paper, only to record the data in the patient's EMR at some later time. This manual transfer of data oftentimes results in error both in accurately recording the data, and recording the data in the correct patient's EMR, as there is no positive verification that the patient from which the data was taken is the same patient to which the EMR belongs. As mentioned, transcription errors are probable, given that this method may take several hours from the time the data is written down or otherwise recorded from the medical device, until the time that it is recorded into the patient's EMR.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Embodiments of the present invention provide systems and methods for efficiently and effectively recording data from a medical device into a patient's EMR. A medical device may be transferred from room to room by a clinician, and associated with various patients such that data can be taken from the medical device that corresponds to the patient who is associated at that time. This data may then be transferred to an application that allows the clinician to edit the data or add other information corresponding to the patient prior to the data being transmitted to the patient's EMR. This process may take a fraction of the time that the manual transfer of data takes, as described above, and is much more efficient than manually entering the data from the medical device into the patient's EMR. In addition to editing or adding other information, a user may verify the data, and then indicate, such as by selecting a designated button, that the data is ready to be transmitted to the patient's EMR. Once the data has been transmitted, the patient and the medical device may be disassociated so that another patient can be identified, and data can be acquired from the medical device that corresponds to the newly associated patient.

More particularly, a first aspect of an embodiment of the present invention includes one or more computer-readable storage media having computer-executable instructions embodied thereon, that, when executed perform a method for electronically transferring data associated with a patient from a medical device to an EMR that corresponds to the patient. The method includes receiving an identification of the medical device, receiving an identification of a first patient, and receiving a user selection to associate the first patient to the medical device. Further, the method includes, in response to receiving the user selection to associate the first patient to the first medical device, acquiring the data associated with the first patient from the medical device, and communicating the data for display in a format that allows a user to manipulate the data. The method additionally includes receiving an indication that the data is to be transmitted to the EMR that corresponds to the patient, and transmitting the data to the EMR that corresponds to the first patient. Upon transmitting the data to the EMR, the method also includes disassociating the first patient and the medical device such that a second patient can be associated to the medical device.

In a second aspect, embodiments of the present invention are directed toward a system having a processor and one or more computer-readable storage media for electronically transferring data associated with a patient from a medical device to an EMR that corresponds to the patient. The system includes a receiving component for receiving identifications for the patient and the medical device, an associating component for associating the patient to the medical device in response to receiving an indication that the patient and the medical device are to be associated, and an acquiring component for acquiring the data from the medical device that is associated with the patient. The system further includes a transmitting component for transmitting the acquired data to a requesting application so that the data can be manipulated prior to being stored in the EMR corresponding to the patient. Additionally, the system includes a publishing component for publishing the data to the EMR that corresponds to the patient in response to receiving an indication that the data is to be transmitted to the EMR.

A further aspect of an embodiment of the present invention takes the form of one or more computer-readable storage media having computer-executable instructions embodied thereon, that, when executed perform a method for electronically transferring data associated with a patient from a medical device to an EMR that corresponds to the patient. The method includes receiving an identification of a first patient, receiving an identification of the medical device, and in response to receiving the identification of the medical device, acquiring the data associated with the first patient from the medical device. Further, the method includes associating the first patient and the medical device to one another, communicating the data for display such that the data can be manipulated by a user, and receiving an indication that the data is to be transmitted to the first patient's EMR. The method additionally includes transmitting the data to the first patient's EMR, wherein once the data is transmitted to the first patient's EMR, the first patient and the medical device are no longer associated.

BRIEF DESCRIPTION OF THE DRAWINGS

Embodiments are described in detail below with reference to the attached drawing figures, wherein:

FIG. 8 is an illustrative screen display showing data acquired from a medical device, in accordance with an embodiment of the present invention;

FIG. 10 is an illustrative screen display showing a patient's EMR after receiving transmitted data from a medical device, in accordance with an embodiment of the present invention;

FIG. 11 is an illustrative screen display showing a method of searching for a patient in a database, in accordance with an embodiment of the present invention;

FIG. 13 is an illustrative screen display showing data acquired from a medical device, in accordance with an embodiment of the present invention.

DETAILED DESCRIPTION

Figure 1:
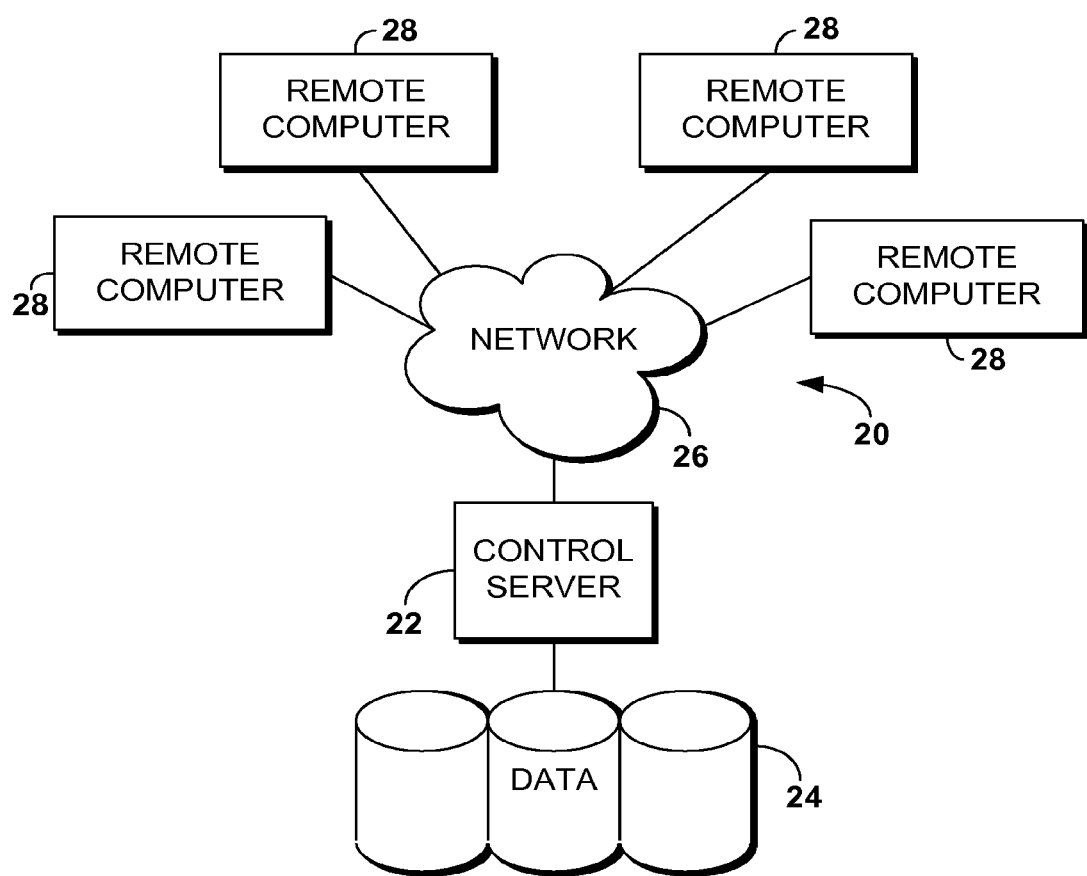
FIG. 1 is a block diagram of an exemplary computing environment suitable for use in implementing embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

The claimed embodiments of the present invention provide an improved electronic medical record system for ensuring the secure and accurate transfer of data associated with a patient and a medical device to an electronic medical record of the specific patient. The claimed embodiments of the present invention work through a specific network architecture to provide positive patient identification, association of the data, patient, and medical device, followed by disassociation upon data transfer completion. These elements improve the security of digital patient information and ensure that the data transmitted to a patient's electronic medical record is related to that specific patient, as transmission to the wrong electronic medical record potentially creates data privacy disclosure concerns. The claimed embodiments enforce positive patient identification and association, and disassociation upon completion. The claimed embodiments, therefore, provide a technical solution to the technical problem of erroneously transmitting one patient's medical information to an electronic medical record of a different patient.

The claimed embodiments of the present invention also provide an improved electronic medical record system for transferring data associated with a patient and a medical device to an electronic medical record, through specific network architecture, including dynamic form building. As discussed later in this Detailed Description, forms are dynamically generated so that a clinician can enrich the data being transferred with their observations. An exemplary form includes a drop-down box that allows the user to fill in additional information for the identified patient, via a graphical user interface. For example, a form is dynamically generated to include a data field box for blood pressure data, the data field box having data transferred to it from the medical device. In such an example, the user may choose to identify how the blood pressure was taken on the patient, such as if the patient was sitting, standing, or supine by adding input to the data field box to enrich the blood pressure data to be transferred to a patient's electronic medical record. Thus, the claims embodiments provide a technical solution to the technical problem of accurate and timely data transfer as further enriched with a clinician's observations. Again, medical devices could not intelligently connect and communicate with a patient's electronic medical record in prior systems.

Having briefly described embodiments of the present invention, an exemplary operating environment suitable for use in implementing embodiments of the present invention is described below.

Referring to the drawings in general, and initially to FIG. 1 in particular, an exemplary computing system environment, for instance, a medical information computing system environment, with which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer-readable media, for instance, database cluster 24. Computer-readable media can be any available media that may be accessed by server 22, and includes volatile and nonvolatile media, as well as removable and non-removable media. By way of example, and not limitation, computer-readable media may include computer storage media and communication media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 22. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 24, provide storage of computer-readable instructions, data structures, program modules, and other data for the control server 22.

The control server 22 may operate in a computer network 26 using logical connections to one or more remote computers 28. Remote computers 28 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the elements described above in relation to the control server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in association with the control server 22, the database cluster 24, or any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) may be utilized.

In operation, a clinician may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 22. In addition to a monitor, the control server 22 and/or remote computers 28 may include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Figure 2:
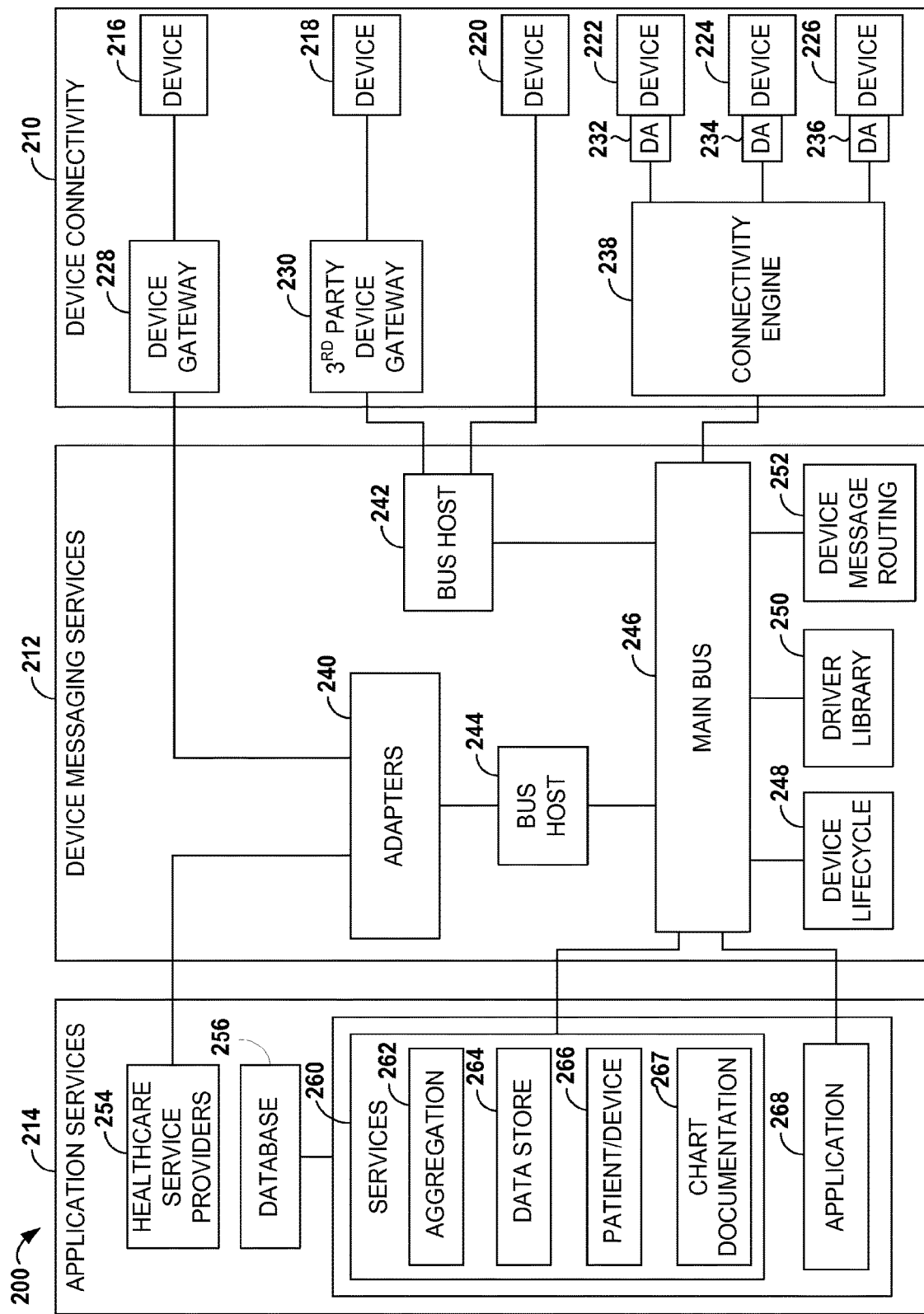
FIG. 2 is an exemplary system architecture suitable for use in implementing embodiments of the present invention.

FIG. 2 is an exemplary system architecture 200 suitable for use in implementing embodiments of the present invention. Generally, the exemplary system architecture 200 advantageously allows for communication with medical devices, for example, through a bus or server, instead of communication directly with the medical devices. A patient to device association may be initiated, and the existence of a bus or server may assist in maintaining that association until the occurrence of a disassociation event. If a computing device, such as a PDA, for example, were to communicate directly with a medical device, the relationship or association between the patient and medical device may terminate when that particular medical device is no longer being used for that particular patient. There may be instances, however, when a caregiver may want the association between that patient and medical device to continue until the occurrence of some disassociation event. In that case, a bus may assist in maintaining and managing that relationship.

Initially, the exemplary system architecture 200 includes device connectivity 210, device messaging services 212, and application services 214. The device connectivity 210 includes one or more medical devices that are connected to the device messaging services 212 such that the devices may, at a later time, be associated to a particular patient and/or an order. These devices may include, but are not limited to monitors, cardiac ventilators, balloon pumps, patient beds, infusion pumps, sequential compression devices, electronic security devices, vital signs devices, or any other device that a health care provider may use for a patient while the patient is in the hospital. These devices are shown in FIG. 2 as areas 216, 218, 220, 222, 224, and 226.

Each medical device may communicate with the device messaging services 212 in a different way. For example, some devices, such as device 216, may utilize a device gateway 228. A gateway is generally a device that connects networks or other devices using different communications protocols so that information can be easily passed from one to the other. A gateway may both transfer information and convert it to a form compatible with the protocols used by the receiving network. Here, the device gateway assists in the transfer of data from the device 216 to the device messaging services 212. As will be described in greater detail below, an adapter, such as adapter 240 may be used in instances where the device gateway 228, was provided by the device manufacturer. The adapter 240 is typically used to facilitate communication from a consumer to the gateway over the consumer's protocol. It should be noted that an adapter may reside on or near the device messaging services, or may reside near the actual device or device gateway. In other instances, a device gateway may be a third-party device gateway 230. In these instances, an adapter may not be necessary, as the device messaging services 212 may already know what type of messages to expect from that device 218 through the third-party device gateway 230. Many different connection types may be utilized between devices, gateway servers, and components of the device messaging services 212, including, but not limited to, HL7 TCP/IP, a software development kit (SDK), RS 232, etc.

Other devices, such as device 220, may have an internal gateway or other component such that a gateway like 228 or 230 would not be needed. These devices may have all of the required capability built into it, and, if necessary, may even have their own adapters incorporated therein such that a separate adapter would not be necessary. Still other devices, such as devices 222, 224, and 226, may be legacy devices that are older and don't have networking built-ins. For example, it may not be possible to plug in a CAT 5 network to the legacy devices, the devices may not have wireless networking capabilities, etc. A serial port may be the only connection mechanism that exists on these devices. For these devices, a connectivity engine 238 and device adapters 232, 234, and 236 may be used.

The device adapter is a hardware device that is affixed directly onto the medical device, and acts as the sole source of identification and connection to the connectivity engine 238. Device adapters 232, 234, and 236 are configurable with device specific information including, but not limited to, manufacturer, device name, device model, port settings, and the like. Device adapters 232, 234, and 236 may use various connection mechanisms to connect to the connectivity engine 238 including, but not limited to, Universal Serial Bus (USB) or Personal Area Network (PAN).

The connectivity engine 238 is a piece of hardware that may be connected to devices 222, 224, and 226 either wirelessly or via a wired connection. In addition to the hardware portion of the connectivity engine 238, a software portion may also be included. Even if there is a wired connection between the connectivity engine 238 and a device, there may still be a wireless connection over a wireless network between the connectivity engine 238 and the device messaging services 212. In one embodiment, both a hardware and software portion of the connectivity engine 238 are located near the medical devices, as shown in FIG. 2. In another embodiment, however, the software portion of the connectivity engine 238 runs on the computing device (e.g., PDA, tablet PC) that is used to display data from medical devices, and may be located logically with the application services 214.

The connectivity engine 238 may also assist in detecting types of devices so that the appropriate driver may be loaded, which may be based on the make and model of the particular device. The connectivity engine 238 may be located on the device messaging services 212 or as part of the device subsystems 210, as illustrated in FIG. 2. The device messaging services 212 or a component thereof may communicate with the connectivity engine 238 to establish a connection to the device itself. In one embodiment, the connectivity engine 238 may be physically present in a patient's room so that when a new device, such as a legacy device, is brought into that room, it may be connected to the connectivity engine 238 if needed. At that time, a connect event may occur, and the device messaging services 212 may broadcast the connect event to other components who may need to know.

The medical devices, either directly or indirectly through a gateway, connectivity engine, or other component are connected to the device messaging services 212. The device messaging services 212, in some embodiments, may generally include one or more adapters 240, one or more bus hosts, such as bus hosts 242 and 244, a main bus 246, a device lifecycle 248, a driver library 250, and a device message routing 252. As previously described, an adapter may be used when the device gateway, such as device gateway 228, is provided by the manufacturer of a device, for example. The adapter 240 assists to facilitate communication from a consumer to the gateway over the consumer's protocol. While one adapter 240 is illustrated in FIG. 2, it is contemplated to be within the scope of the present invention that more than one adapter 240 may be used. In one embodiment, one adapter 240 may be used for more than one medical device, but in another embodiment, each medical device requiring an adapter may require a separate adapter. Further, the adapter 240 may be used to communicate data from the device messaging services 212 to healthcare system providers 254. In these cases, the data may not be transferred through any services or applications, but may be transferred directly to other healthcare system providers 254. Typically, an inbound and outbound adapter would be provided to transform messages to and from a standard format and protocol, such as HL7.

A bus host, such as bus host 242 or 244 may be used to perform several functions, including, but not limited to, detecting hardware that is plugged in or directly connected to the host, loading appropriate device drivers after the device has been identified, dynamically locating and installing drivers if the driver is not currently present on the host, and for unloading the device driver after the device has been disconnected. A bus host may not be utilized for each and every medical device, but may be used for some that don't have device adapters, for example, which perform many of the functions listed above. The embodiment of FIG. 2, for example, has a bus host for devices 216, 218, and 220, which are not shown as having device adapters, such as device adapters 232, 234, and 236, nor do they require use of the connectivity engine 238. In addition to the above described functionality of the bus hosts 242 and 244, they may also allow for communication to the device to get various types of information to and from the device. This information may be, for example, determining whether the bed rails are up or down, or even determining the patient's weight when the patient is sitting or lying on the bed.

The main bus 246 provides connection framework, as it may create and manage all connections to the device messaging services 212. The main bus 246 also provides messaging architecture for the device messaging services 212. The main functionality of the main bus 246 includes providing general operational and management capabilities for connected devices, which may vary depending on the service that is subscribing or requesting the data from the devices.

A device lifecycle 248 may detect the presence of a device on the main bus 246. The device lifecycle 248 also may maintain an accurate directory of currently connected medical devices to the main bus 246 as various medical devices become connected. Further, it may ensure "active" connectivity of a medical device to the main bus 246 via a device heartbeat. A heartbeat is an indication given at a certain interval of time that a particular medical device is connected to the main bus 246. This interval may vary, and may be regular, such as every 20 seconds, for example. Additionally, the interval may depend on each medical device. As a medical device deregisters, or becomes unconnected to the main bus 246, the device lifecycle 248 may be responsible for sending out a notice of a disconnect event, and will then stop sending that device's heartbeat out to certain components that require that information. There are various phases of the device lifecycle 248, which may include, in one embodiment, a notification phase that notifies of an event generated at the device connection and of a device connected as directly to the main bus 246; an interrogation phase; an identification phase that identifies the vendor, make, model, etc. of each medical device and that finds and downloads the appropriate driver when necessary; an activation phase that loads the device driver and registers the medical devices; and an execution phase that is responsible for tracking the medical devices' heartbeats and gathers and transmits data to and from the medical devices.

A driver library 250 may store a plurality of drivers that may be used and installed on particular devices, when required. Further, a device message routing component 252 handles routing messages from source to destination across the device messaging services 212. Messages may take on a variety of forms, and may contain vastly different types of content. Various types of messaging may include request and reply messaging, publish and subscribe messaging, and asynchronous one-way messaging. Request and reply messaging includes taking a message from a source, routing it to a single destination, and routing a reply message from the destination back to the original source. Publish and subscribe messaging involves a publisher sending messages out on a named topic, which may be received by multiple subscribers. Asynchronous one-way messaging includes doing requests and reply messaging without needing to receive a reply. The only receipt message may be an indication that the message was successfully sent.

With continued reference to FIG. 2, application services 214 includes various components, including healthcare system providers 254, a database 256, services 260, and an application 268. The services 260 may consume some or all of the information that the main bus 246 provides. In some instances, the services 260 may be application programming interfaces (APIs), which may support requests made by computer programs, such as applications. For instance, the services 260 may use the main bus 246 to determine where a connected device is located. The services 214 may include various components that may all utilize information sent by the main bus 246. These may include, for example, an aggregation component 262, a data store 264, and a patient to device association 266, which is further discussed herein. The aggregation component 262 allows for a user to query a patient by a patient identification over a large number of patient identifications. Once a match is found, information relating to that patient, such as devices that the patient is associated with, may be retrieved. The data store 264 stores data that is published by the medical devices.

In various embodiments of the present invention, the services 260 run on the main bus 246, and thus together with the main bus 246, may provide additional functionality to the system as a whole. For example, when various services 260 run on the main bus 246, the main bus 246 may store discrete data posts, such as heart rate, systolic blood pressure, diastolic blood pressure, etc., in a data store, such as data store 264, for historical queries and archiving. Further, the main bus 246 may chart acquired discrete data into a patient's EMR; publish medical device outcomes, such as lab results and other test results, to a patient's EMR; and publish digital media from a device into a patient's EMR, publish infusion data, if required, and infusion events (e.g., infusion rate, volume infused, volume to be infused, rate change, begin bag, end bag) into a patient's EMR.

The application 268 works with the services 260 to facilitate specific functionality, such as chart documentation. The application 268, in one embodiment, may be a user interface, such as the user interfaces illustrated in many of the figures associated with this application. Here, the user interfaces may be screen shots of associating a patient to a device, or to an order, for example. While one application 268 is illustrated in FIG. 2, more than one application is considered to be well within the scope of the present invention. The services 260 and the application 268 are incorporated such that the services 260 retrieve raw data from the main bus 246 and other components, while the application 268 uses that information and presents it to a user through a user interface.

While only a main bus 246 is illustrated in FIG. 2, more than one bus may be used in implementing embodiments of the present invention. By way of example only and not limitation, the main bus 246 may be a first bus that is responsible for managing all of the medical devices. This main bus 246 may be located at the facility, such as a hospital. One or more local busses may be present that can store and facilitate the transfer of information from one or more medical devices, and that transfer that information to the main bus 246. The main bus 246 may not even be aware that there are local busses, as the local busses may just be proxying messages that they receive from the medical devices. Local busses may also be present at the facility (e.g., hospital), but may be physically located in a patient's room, for example, such as on a cart where an associated medical device is located. In one embodiment of the present invention, more than one main bus 246 may be available to provide a backup system. One main bus may be a primary node, and the other may be a secondary node. If one node goes down, the secondary node may be utilized. Additionally, the nodes or busses may be used in conjunction with one another such that each has certain responsibility, for example.

The database 256, in one embodiment, may be sent patient, medical device, and order association information. For instance, identification of a patient and medical device that have been associated may be sent to the database 256. Any data that it released by the medical device may also be routed to the database 256 so that this information can be stored in a flowsheet, for example. A clinician may then make the decision as to what to do with the data. For example, the clinician may decide that certain data points should be included in the patient's chart, and the others may be completely deleted from the database 256. A specific example of this may be when a clinician looks at data in the database 256 that is associated with a certain patient. The data may include values at different times, such as 12:00 PM, 12:15 PM, and 12:30 PM. The clinician may not wish for all of these values to be entered into the patient's chart, but may choose, for example, just the 12:00 PM and 12:30 PM entries to officially document. Additionally, having this information in the database 256 allows for a higher accuracy. In one instance, a clinician may write down in a patient's chart that an infusion pump began at 12:10 PM, when it actually started at 12:06 PM. Having this information in the database 256 allows for the clinician to officially document accurate start and end times, as well as other values whose accuracy is important to the patient's health.

As previously discussed, various healthcare system providers 254 may wish to receive data or information regarding a particular medical device or patient. In this case, the adapters 240 may be configured to send this information via an HL7 or ASTM connection, for example, to the healthcare system providers 254. In one embodiment, the services 260 may communicate with various healthcare system providers 254, and this communication takes place via the main bus 246.

Figure 3:
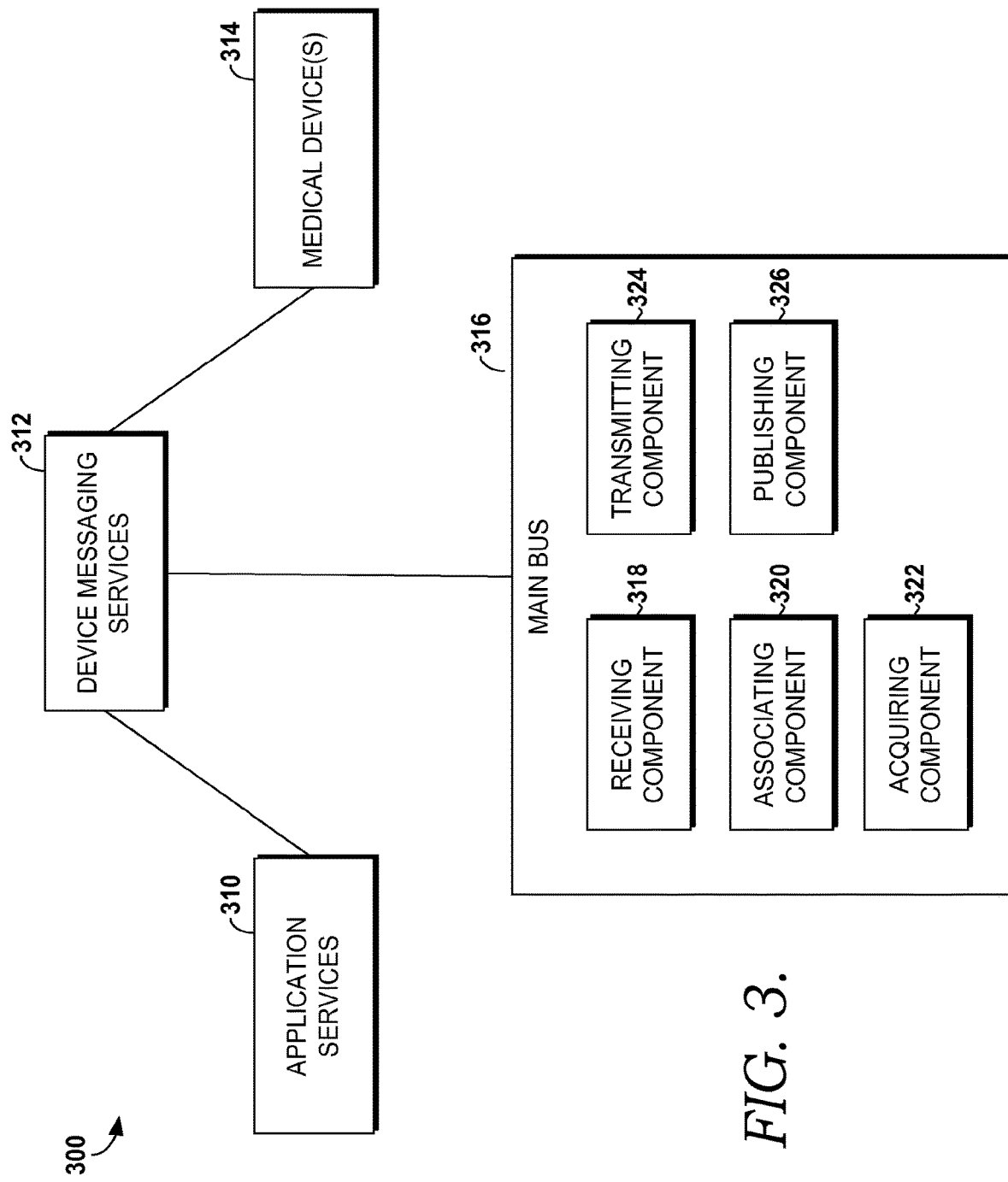
FIG. 3 is a block diagram of an exemplary system, in accordance with an embodiment of the present invention.

Turning now to FIG. 3, a block diagram is shown of an exemplary system 300, in accordance with an embodiment of the present invention. The exemplary system 300 initially includes application services 310, which may comprise several components, such as a database, various services that request and utilize data from medical devices (e.g., aggregation service, data store service, patient to device association services, chart documentation service), and various applications on which the services run. Application services 310 is described in further detail in the discussion of FIG. 2 herein. Device messaging services 312 may include a main bus, which is a central bus or server that is responsible for receiving and delivering data from medical devices to various applications and services. Device messaging services is also described in further detail in the discussion of FIG. 2 herein. Medical devices 314 may include any medical devices and associated components (e.g., device gateways, connectivity engine, device adapters) that are or may be connected, directly or indirectly, to the main bus, such as main bus 246 in FIG. 2.

The main bus 316, as described above, includes a plurality of components, each being responsible for tasks associated with providing data from the medical devices to various services and applications. The main bus 316 includes a receiving component 318, an associating component 320, an acquiring component 322, a transmitting component 324, and a publishing component 326. While these five components are included in the embodiment of FIG. 3, it will become apparent to one of ordinary skill in the art that any number of components, either more or less than the illustrated five, may be used to accomplish the purposes of the present invention. Therefore, other components are contemplated to be within the scope of the present invention. For example, a displaying component may be includes that communicates the data for display such that the data can be manipulated by a user.

The receiving component 318 receives identifications for the patient and the medical device. The identifications may be received in a number of ways, including, but certainly not limited to, scanning a barcode associated with the patient or the medical device, entering a name or identification associated with the patient or medical device, or searching an electronically searchable database for a patient or medical device. Further, more than one patient or medical device may be identified.

The associating component 320 associates the identified patient and the identified medical device in response to receiving an indication that the patient and the medical device are to be associated. This indication may take many forms. An explicit association may be available to the user, such as through a selectable button on the display device. Alternatively, an implicit association, such as a button that allows the user to acquire data from the medical device, may be available to the user. In one embodiment, once that button is selected, the identified patient and medical device may be associated, prior to or simultaneous to receiving data from the medical device.

The acquiring component 322 acquires the data from the medical device that has been associated to the identified patient. The acquiring component 322 may request the data from the medical device from which it requires the data. The medical device, in one embodiment, may send the most recent data that it has for the patient to the acquiring component 322.

The transmitting component 324 transmits the acquired data to a requesting application or service so that the data can be manipulated prior to being stored in the EMR corresponding to the patient. For instance, the chart documentation services 267 application may have requested the data. Alternatively, in one embodiment, the main bus 316 or a component thereof (e.g., the transmitting component 324) may request the data from the medical device, and may send the data to an application or a service, such as the chart documentation services 267, without having received a request for the data by the application or service. That application or service may store the data in a format such that a user has the capability to manipulate or edit the data prior to the data being transmitted to the patient's EMR, where the data is indefinitely stored for future reference. For instance, the data transferred to the application or service may be vital information for a patient, but a clinician may wish to update one or more of the values manually, and as such, may be able to edit the one or more values in the application or service. Further, one or more fields, such as drop-down fields that have options from which a user may select, may be intentionally left blank for a user, such as a clinician, to complete.

The publishing component 326 publishes, or transmits the data to the EMR that corresponds to the patient in response to receiving an indication that the data is to be transmitted to the EMR. As previously mentioned, a user, such as a clinician, may have the opportunity to review the acquired data in a format that allows the user to edit the data, if desired. Once the information has been reviewed and has been determined to be accurate, and once the user has had the opportunity to edit or add any other information, the user may select a button, such as a sign button, that indicates that the data is ready to be transmitted or published to the patient's EMR.

Figure 4:
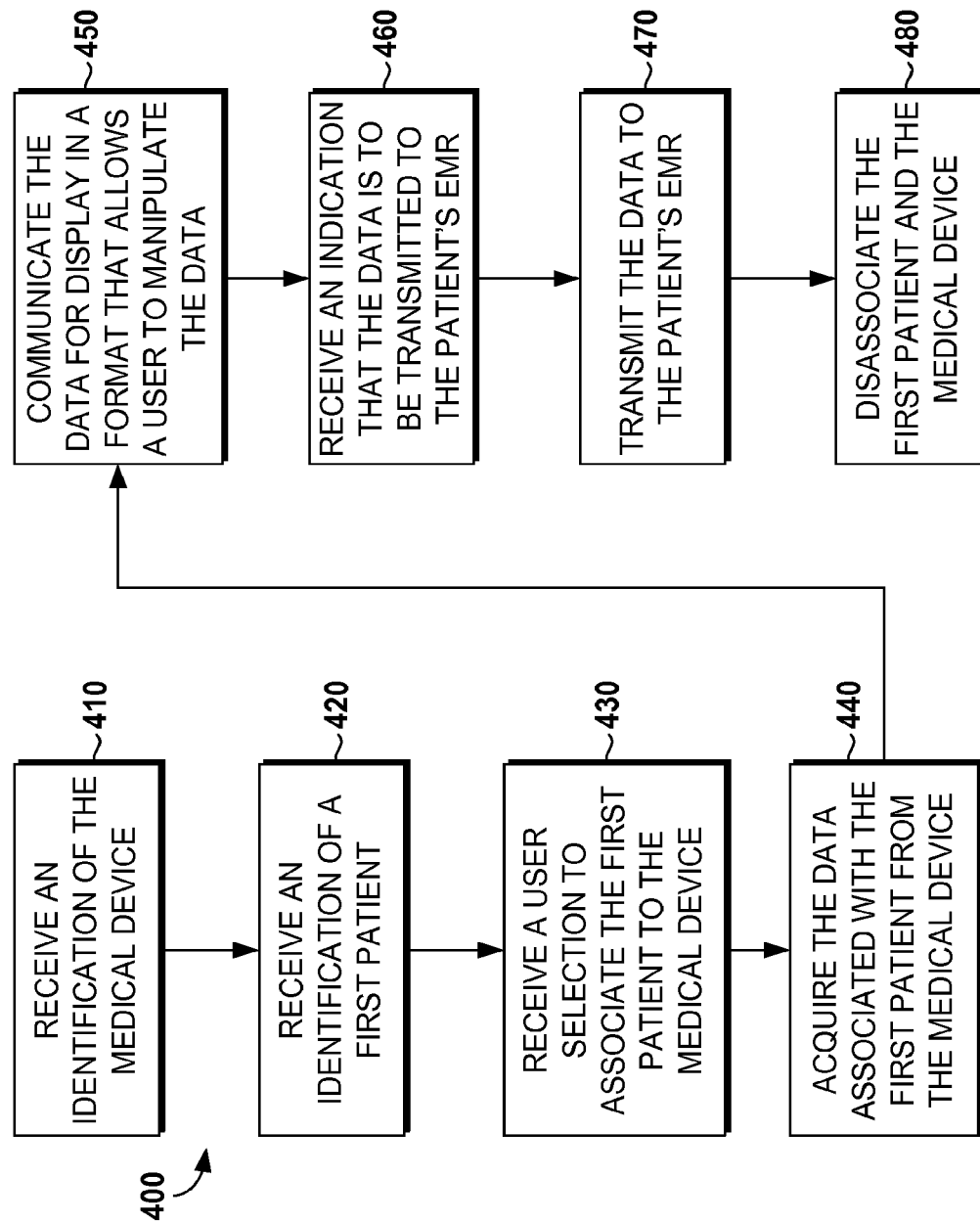
FIG. 4 is an illustrative flow diagram of a method for electronically transferring data associated with a patient from a medical device to an electronic medical record (EMR) corresponding to a patient, in accordance with an embodiment of the present invention.
Figure 6:
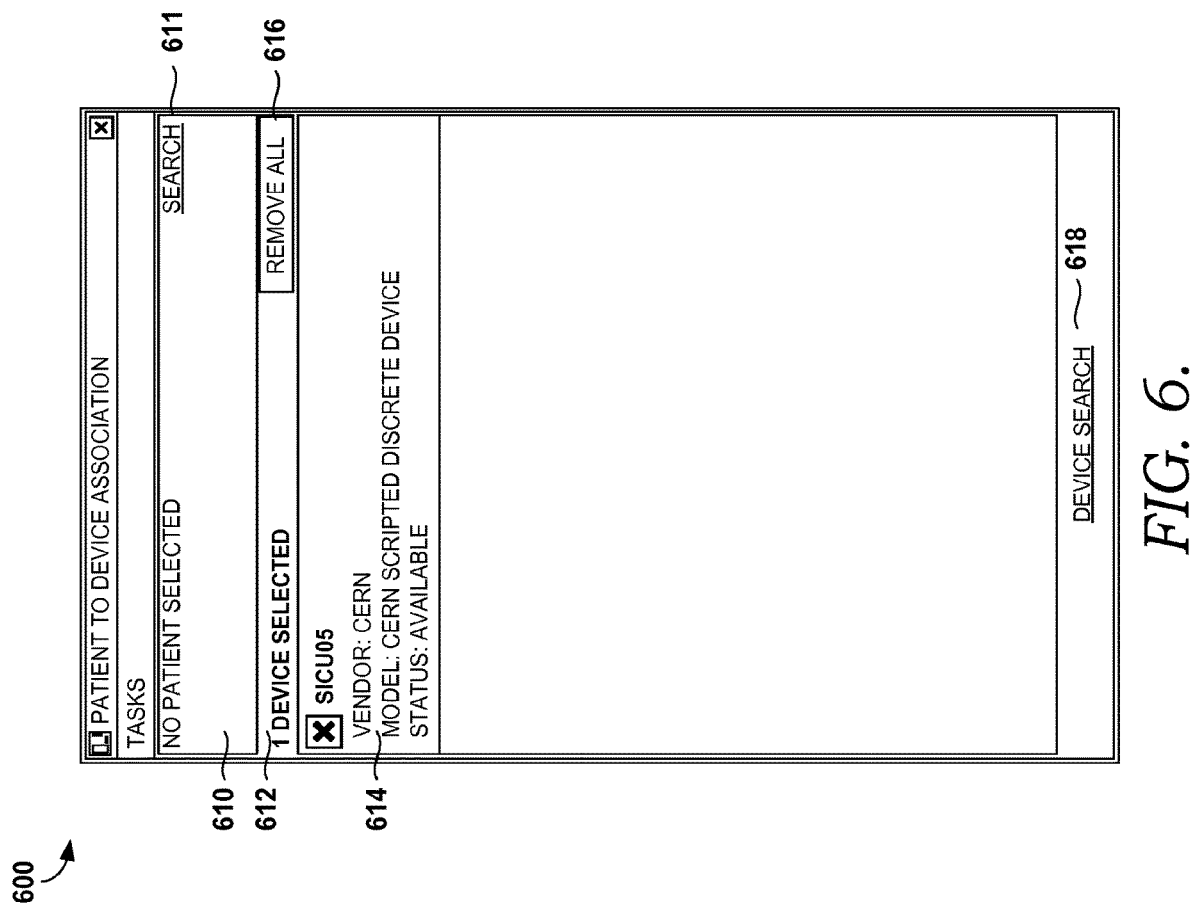
FIG. 6 is an illustrative screen display showing a selected device, in accordance with an embodiment of the present invention.

FIG. 4 is an illustrative flow diagram of a method 400 for electronically transferring data associated with a patient from a medical device to an EMR corresponding to a patient, in accordance with an embodiment of the present invention. Initially, at step 410, an identification of the medical device is received. For example, FIG. 6 illustrates a screen display 600 showing a selected device, in accordance with an embodiment of the present invention. Area 610 indicates that a patient has not yet been selected, or identified, and a search button 611 is provided to allow a user to search in an electronically searchable database for a particular patient. Medical devices may be identified in a number of ways, including, but not limited to, scanning a barcode associated with the device, entering a name or identification associated with the device, or searching an electronically searchable database for a medical device, as mentioned above. Area 612 indicates that one device has been selected or identified, and at area 614, various types of information associated with the identified medical device are displayed. This information includes, but is not limited to, vendor, model, and status information associated with the device.

In one embodiment, a medical device is scanned (e.g., using a barcode associated with the device) or otherwise identified, but the information displayed in area 614 indicates that the medical device is associated or currently being used by another patient. The user, in this case, may have the option to change the association from the currently associated patient to the identified patient, or may choose to select a different medical device, such as by removing all selected devices by using a remove all button 616, and by selecting a device search 618 button. As mentioned previously, selecting the device search 618 button is just one way of identifying a medical device. As illustrated, each device has a box that can be checked, as is illustrated in the embodiment of FIG. 6.

Figure 7:
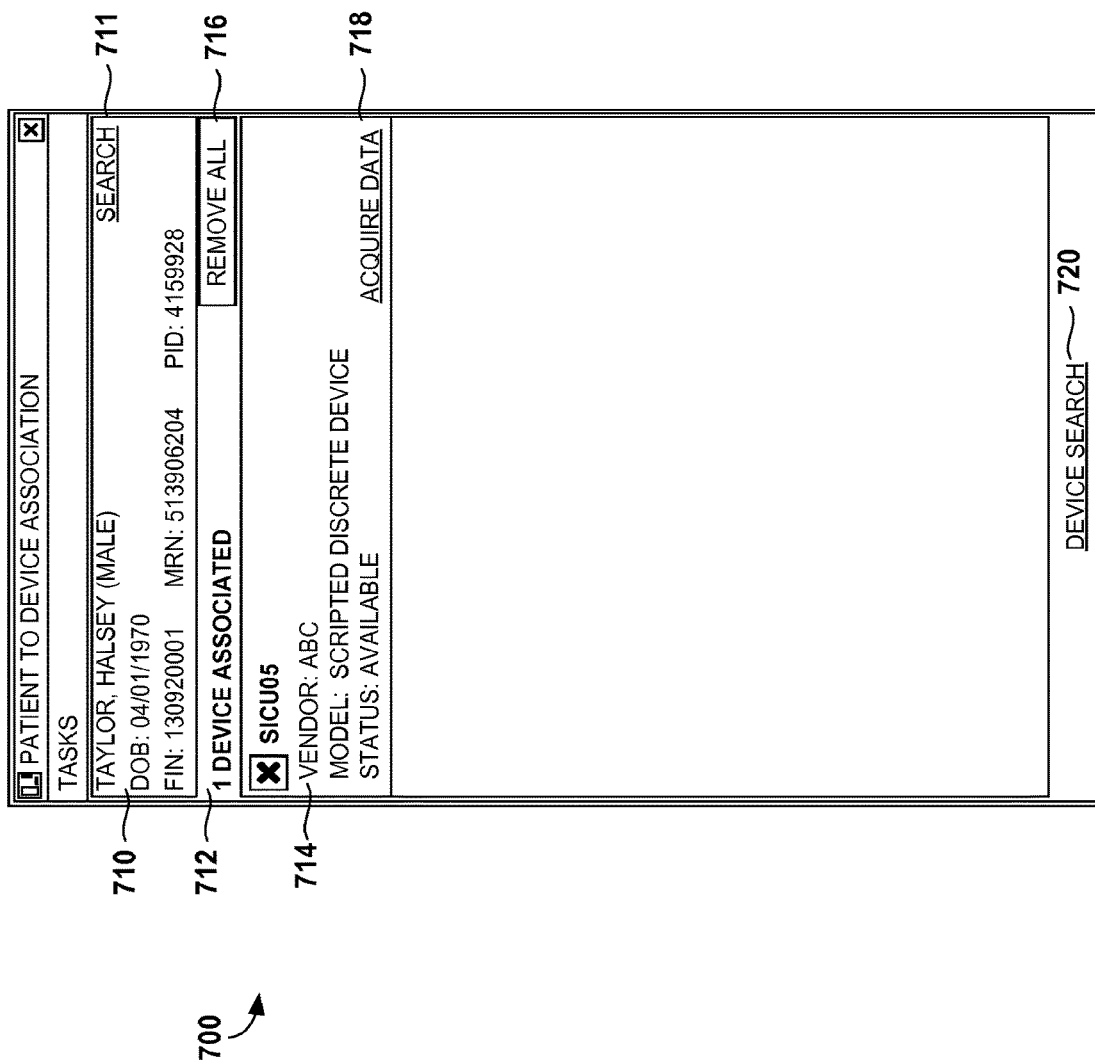
FIG. 7 is an illustrative screen display showing a selected patient and a selected device that have been associated, in accordance with an embodiment of the present invention.

Returning to FIG. 4, at step 420, an identification of a first patient is received. This identification may be received in a number of ways, including, but certainly not limited to, scanning a barcode associated with the patient, entering a name or identification associated with the patient, searching an electronically searchable database for a patient, etc. Further, more than one patient may be identified. To illustrate the identification of a patient and a medical device, FIG. 7 is provided. FIG. 7 illustrates a screen display 700 showing an identified patient and an identified medical device, in accordance with an embodiment of the present invention. The patient is identified, as shown in area 710. In addition to displaying the patient's name, the patient's date of birth, identification numbers, and gender are also displayed. Other embodiments may include other information that assists in identifying the patient. Another patient may be searched for by using a search button 711, as mentioned above. Once the device is associated, as indicated by area 712, and descriptive information for this medical device is displayed in area 714, including vendor, model, and status information. Other embodiments may include different information. The medical devices that have been selected (e.g., the box has been checked) may be removed by selecting the remove all button 716.

Once the medical device and patient have been identified, a user may select an acquire data button 718 that retrieves data (e.g., via the acquiring component 322) from the identified medical device and loads it into an application or service so that the user is able to manipulate the data, if necessary. At area 720, a user may select the device search button 720, which provides one way of identifying a medical device. More than one medical device may be identified and displayed on a screen display, such as the screen display 700.

Returning to FIG. 4, at step 430, a user selection to associate the first patient to the medical device is received. This user selection may take the form of a user selecting a button that indicates that the user wishes to receive data corresponding to the first patient from the medical device, such as the acquire data button 718 in FIG. 7, discussed above. Prior to or simultaneous to receiving the data, the first patient and the medical device may be associated. In response to receiving the user selection to associate the first patient and the medical device to one another, the data associated with the first patient is acquired from the medical device at step 440. At step 450, the data is communicated for display in a format that allows a user to manipulate the data. For example, FIG. 8, illustrates a screen display 800 showing data acquired from a medical device, in accordance with an embodiment of the present invention. The patient is identified in area 810, and a search button 811 is provided as one way of identifying a new patient. Area 812 identifies the associated device, and in area 814, the data acquired from the device is displayed.

In the embodiment of FIG. 8, vital information was taken for the identified patient, which includes diastolic blood pressure, systolic blood pressure, heart rate, temperature, and pulse rate. Although vital information is shown in FIG. 8, any other type of data than can be acquired from a medical device is contemplated to be within the scope of the present invention. As previously mentioned, data may be edited or added prior to being transmitted to the patient's EMR. For instance, the data transferred to an application or service may be vital information for a patient, such as is shown in FIG. 8, but a clinician may wish to update one or more of the values manually, and as such, may be able to edit the one or more values in the application or service. Further, one or more fields, such as drop-down fields that have options from which a user may select, may be intentionally left blank for a user, such as a clinician, to complete.

For example, several data field boxes are left blank in FIG. 8, so as to allow a user to fill them in. Further, the data fields may be defined by the user, such that if the user finds it necessary to add an additional data field that is not currently displayed, the user can add the additional data field(s) to add more information. Here, data field box 816 is an example of a box that has had data transferred to it from the medical device, and data field box 818 is an example of a box, here a drop-down box, that allows the user to fill in additional information for the identified patient. For instance, the user may choose to identify how the blood pressure was taken on the patient, such as if the patient was sitting, standing, or supine. Another drop-down box may be available to identify where the temperature was taken on the patient, such as orally, rectally, in the ear, under the arm, etc. Other examples of data fields in the embodiment of FIG. 8 that allow a user to fill in additional information include the respiratory rate of the patient, or a pain scale of the patient. As previously mentioned, the user has the option to customize the displayed data fields.

Area 820 displays the time and date when the data was acquired from the medical device. At any time, a user may be able to get the most updated data from the medical device by selecting a reacquire data button, such as button 822. The information in areas 814 and 820 may be updated when data is reacquired. As mentioned, once the user has verified the information, a sign button 824 may be selected, and the data can then be transmitted to the patient's EMR, as will be described in more detail below. Although a sign button is provided in the embodiment of FIG. 8, other methods of indicating that the data is to be sent to the patient's EMR are contemplated to be within the scope of the present invention.

Returning to FIG. 4, at step 460, an indication that the data is to be transmitted to the patient's EMR is received, and the data is transmitted to the patient's EMR at step 470. Once a user, such as a clinician, has verified that the data from the medical device is accurate, and had edited or added information as needed, the user indicates (e.g., sign button 824 of FIG. 8) that the data is ready to be transmitted to the patient's EMR for future retrieval. At this point, the data has been authenticated by the user. At step 480, upon transmitting the data to the first patient's EMR, the first patient and the medical device are disassociated such that a second patient can be associated to the medical device. This disassociation may not be an explicit disassociation, but may be an implicit disassociation, wherein the patient's identification is automatically removed from the screen display without receiving an explicit indication from a user that the patient and medical device should be disassociated.

Figure 9:
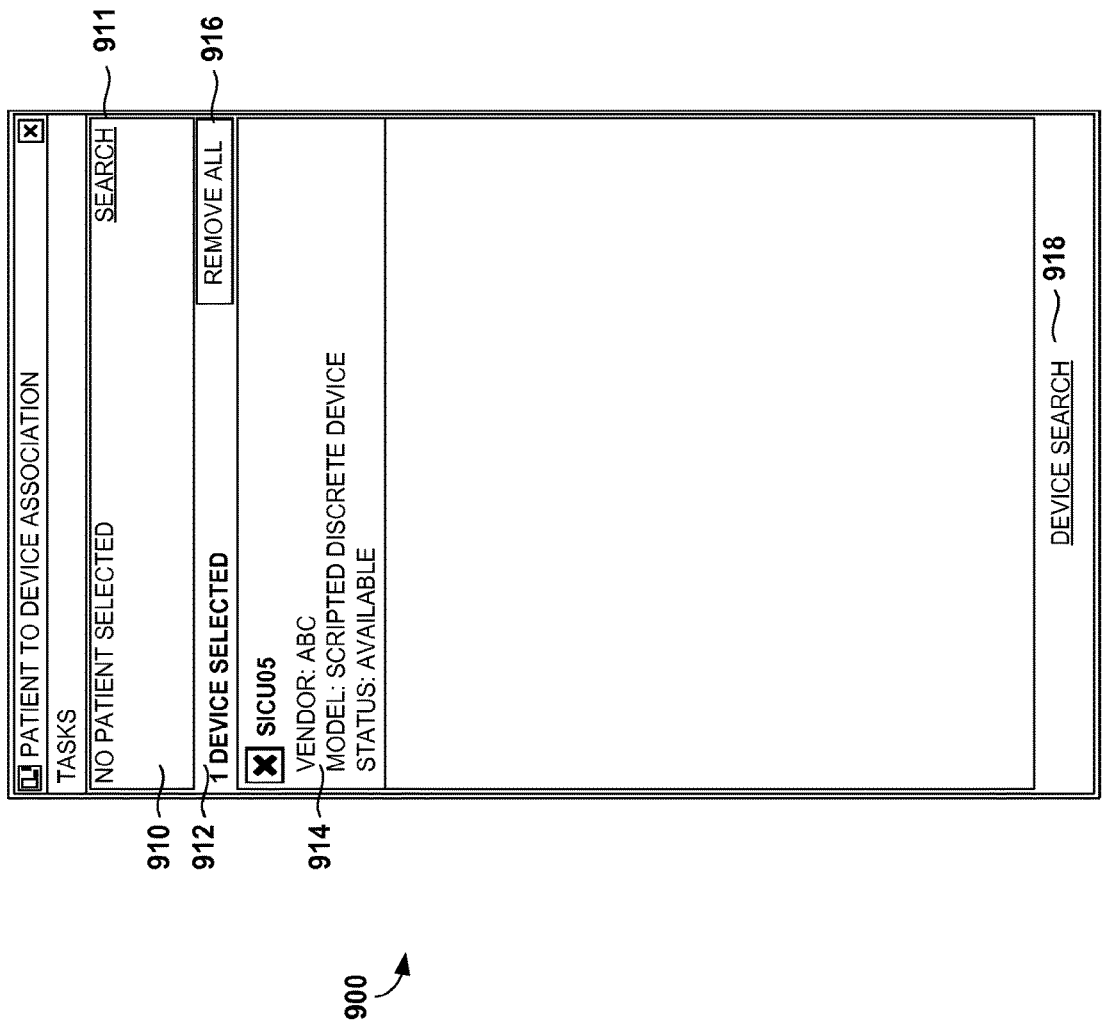
FIG. 9 is an illustrative screen display showing a patient having been disassociated from the medical device upon data associated with the patient having been transmitted to the patient's EMR.

In one embodiment, once the data from the first patient is transmitted to that patient's EMR, the disassociation occurs, thereby allowing for another patient to be identified and associated to the same medical device. In one instance, the medical device does not need to be identified again. An illustrative embodiment of this is shown in FIG. 9, which is an illustrative screen display 900 showing a patient having been disassociated from the medical device upon data associated with the patient being transmitted to the patient's EMR.

Initially, area 910 illustrates that no patient has yet been selected, as the last patient that was associated with the device has been removed and automatically disassociated. Area 912 indicates that one device, which is the same device, is still selected. Information for the medical device is shown in area 914. A new patient may be identified in any of the ways described above, including the use of a search button 911 for searching an electronically searchable database having a plurality of patients, such as patients that are currently admitted in a particular hospital, or patients of a particular doctor's office. If another device is desired, the remove all button 916 may be selected to remove one or more devices that have been selected (e.g., by checking the checkbox), and the device search button 918 may be selected to search for another device. As previously mentioned, other methods for identifying a device may also be available.

As mentioned above, at step 470, the data is transmitted to the patient's EMR. FIG. 10 illustrates a screen display 1000 that shows a patient's EMR after receiving transmitted data taken from a medical device, in accordance with an embodiment of the present invention. Area 1010 contains information about the patient to which the EMR belongs. An information display portion 1012 of the screen display 1000 illustrates the data that was transmitted from the application or service to the EMR. For instance, the patient's vitals are shown in the embodiment of FIG. 10, as the medical device associated to the patient was a device that takes vitals. Thus, a temperature, heart rate, pulse rate, and blood pressure are displayed in the patient's EMR. Here, the patient's vitals were taken at three separate times: first at 2:25 PM as indicated in area 1014, a second time at 2:27 PM as indicated in area 1016, and a third time at 2:32 PM as indicated in area 1018. In one embodiment, a user may identify a patient three separate times to record vitals at three separate times in the patient's EMR, but in another embodiment, the user may be able to identify, and therefore associate the patient to the medical device one time, and continue taking readings from the medical device, and have all of the data transmitted to the patient's EMR.

In one embodiment, an identification of a second patient is received, and a user selection is received to associate the second patient to the medical device. As mentioned, this indication may be the selection of a button, such as an acquire data button, or a link, that acts as a retrieval mechanism that retrieves the data from the medical device. The data associated with the second patient is then acquired from the second medical device. This process may continue with a third patient, a fourth patient, etc.

In still another embodiment, one or more medical devices may be suggested to the user. The medical devices may be suggested based on a number of factors. The user may then select one of the suggested medical devices, and that user selection is received. The patient and the selected device may be associated, and the data associated with the first patient may be acquired from the selected medical device. The medical devices may be suggested based on, for exemplary purposes only, a location of the patient. For instance, the patient may be located in the intensive care unit (ICU) of a hospital, and medical devices typically used in the ICU may be suggested. Alternatively, the medical devices may be suggested based on a diagnosis or treatment of the patient. Still yet, the medical devices may be suggested based on one or more demographics of the user, such as the user's age, gender, or the like.

Figure 5:
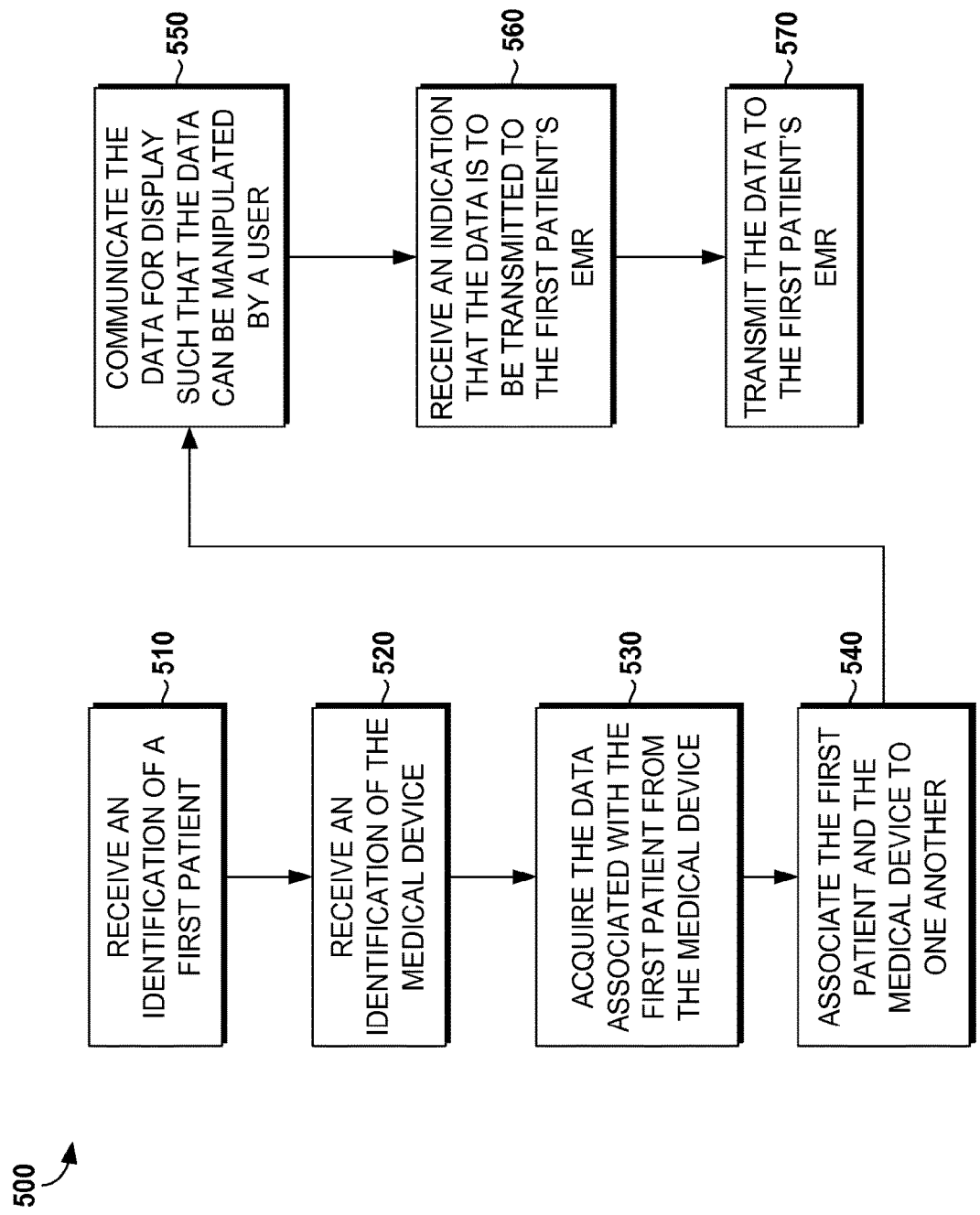
FIG. 5 is an illustrative flow diagram of a method for electronically transferring data associated with a patient from a medical device to an electronic medical record (EMR) corresponding in accordance with an embodiment of the present invention.
Figure 12:
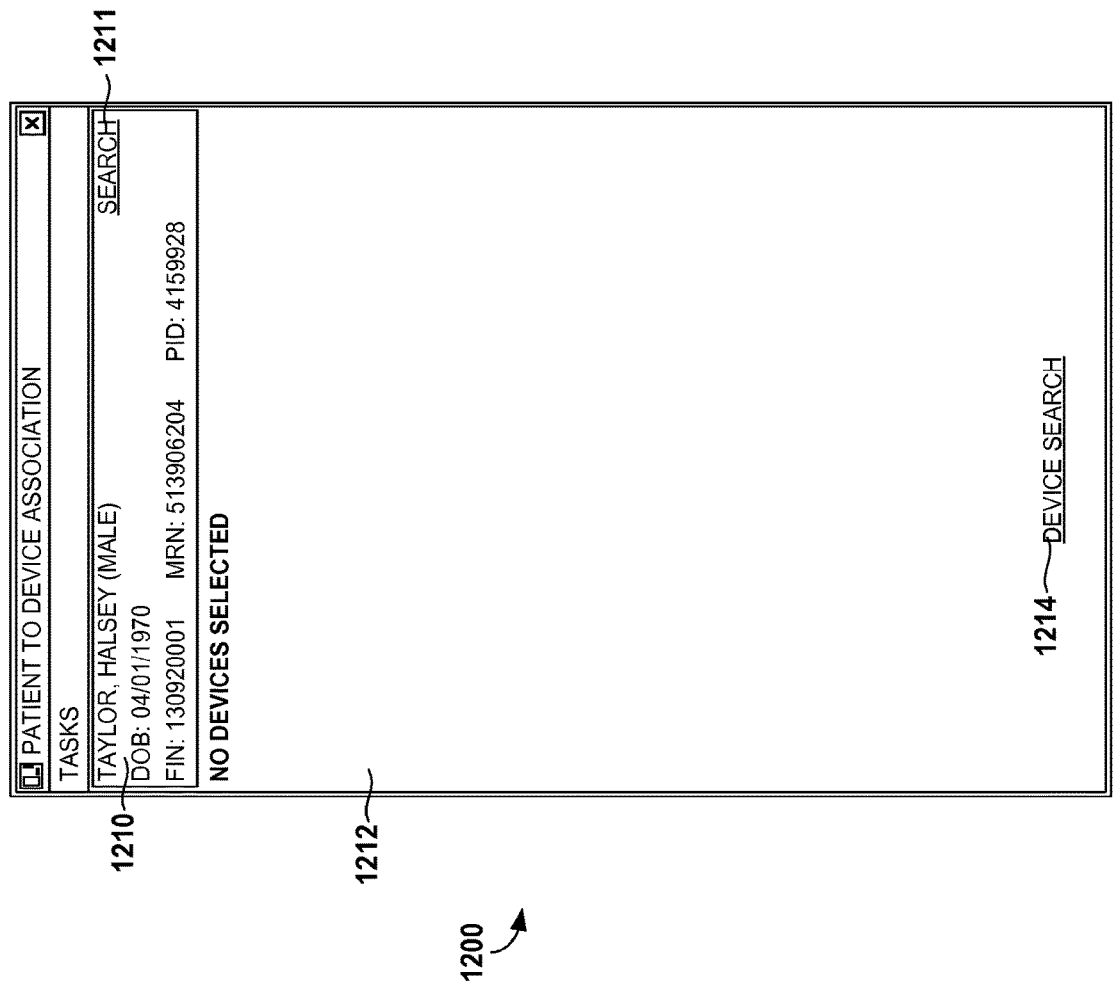
FIG. 12 is an illustrative screen display showing an identified patient, in accordance with an embodiment of the present invention.

Turning now to FIG. 5, an illustrative flow diagram is shown of a method 500 for electronically transferring data associated with a patient from a medical device to an electronic medical record (EMR), in accordance with an embodiment of the present invention. While FIG. 4, as described above, illustrates a user first identifying a medical device followed by a patient, FIG. 5 illustrates first identifying a patient, and then a medical device. Thus, initially, at step 510, an identification of a first patient is received. FIGS. 11 and 12 further illustrate the identification of a patient. For example, FIG. 11 is an illustrative screen display 1100 showing a method of searching for a patient in a database, in accordance with an embodiment of the present invention. This is just one method of identifying a patient, and others are contemplated to be within the scope of the invention. Here, a patient may be searched for utilizing the search box, shown by area 1110. The search may be performed using the patient's name (e.g., first name, last name) or the patient's identification number, and by selecting a search button 1114. Area 1112 is a patient list area that displays the patients that are found in the database, and may include some information about the patient that may assist in verifying that the correct patient is identified. As shown here, gender and date of birth information is displayed for one or more of the patients.

Once a patient has been identified by one of many available methods, information corresponding to the patient may be displayed on a screen display, as illustrated by FIG. 12. FIG. 12 is an illustrative screen display 1200 showing an identified patient, in accordance with an embodiment of the present invention. The patient information, such as the patient's name, date of birth, and identification number(s), is displayed in area 1210. Area 1212 indicates that no device has yet been selected, and a device search button 1214 is provided as one method for identifying a medical device.

Referring back to FIG. 5, an identification of a medical device is received at step 520. In the embodiment of FIG. 5, the identified medical device and related information (e.g., vendor, model, status) may not be displayed, but the data from the medical device corresponding to the identified patient may be immediately acquired and displayed. Thus, unlike the embodiment of FIG. 4, it is not required here that the user select an acquire data button to associate the patient and medical device and to acquire the data, as once the medical device is identified, the data may be displayed.

Figure 13:
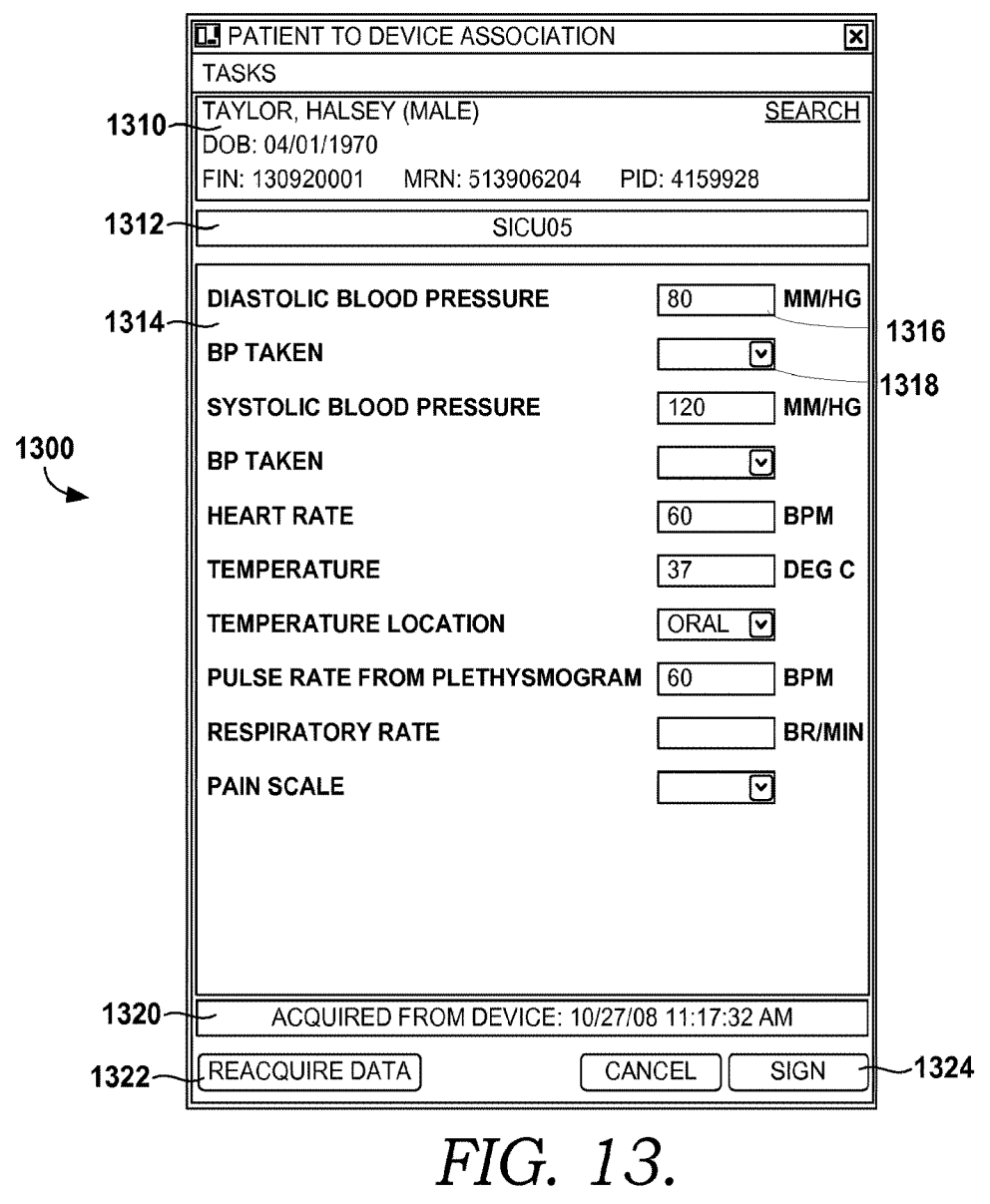

At step 530, the data associated with the first patient is acquired from the medical device in response to receiving the identification of the medical device. The first patient and the medical device are associated to one another, as shown at step 540. At step 550, the data is communicated for display such that the data can be manipulated by a user. FIG. 13 illustrates a screen display 1300 that shows data acquired from a medical device, in accordance with an embodiment of the present invention. The patient is identified in area 1310, along with patient information, such as the patient's date of birth, and one or more identification numbers. At area 1312, the medical device from which the data has been acquired is identified. The acquired data is displayed in area 1314. In this embodiment, the medical device took vital information from the patient, and thus vital information is displayed in the area 1314. The area 1314 includes information such as diastolic blood pressure, systolic blood pressure, heart rate, temperature, pulse rate, etc. This data acquired from the medical device is shown in data fields, such as data field 1316.

Other data fields are shown, such as item 1318, which has been intentionally left blank for the user, such as a clinician, to fill in. These data fields include how the blood pressure was taken (e.g., sitting, standing, supine), where the temperature was taken on the patient's body (e.g., oral, rectal, from the ear, under the arm), the patient's respiratory rate, and pain scale. These fields, although illustrated in the embodiment of FIG. 13, may be customizable by the user, and thus other embodiments of the present invention may include different data fields for the user to fill in. Area 1320 displays when the data was acquired from the device, and may include information such as a date and time. At any time, the user may request to have the most updated data sent from the medical device by selecting a reacquire data button 1322. In this instance, a user selection may be received to obtain updated data associated with the patient from the medical device. The updated data may be acquired from the medical device, and the data may be communicated for display such that the updated data can be manipulated by the user in a similar manner as the initial data.

An indication that the data is to be transmitted to the first patient's EMR is received at step 560. This indication may take one of many forms. For example, returning to FIG. 13, once the user has verified the data and added or edited any information as necessary, a sign button 1324 may be selected, which provides an indication that the data is ready to be sent to the patient's EMR. At this point, the data has been authenticated by the user. At step 570, the data is transmitted to the first patient's EMR. In one embodiment, once the data is transmitted, the first patient and the medical device are no longer associated. This disassociation of the patient and the medical device may not be explicit, but may be implicit, such that the user doesn't have to provide any indication that they are to be disassociated. In another embodiment, an explicit disassociation is required to disassociate the patient and the medical device, wherein the user has to actively select a button or otherwise provide an indication that the patient and medical device are to be disassociated.

Figure 14:
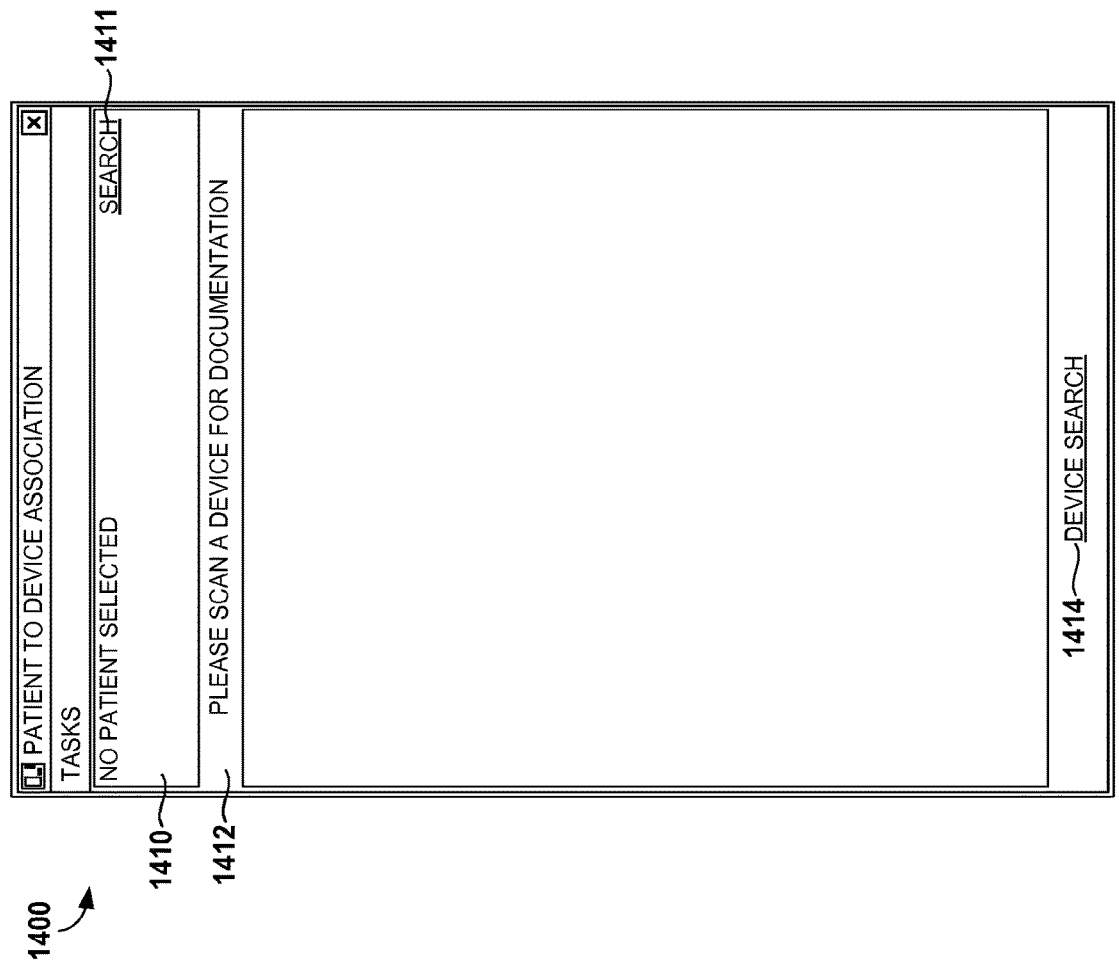
FIG. 14 is an illustrative screen display showing a previously identified patient and medical device having been disassociated and deleted from the display, in accordance with an embodiment of the present invention.

In a further embodiment, which is illustrated in FIG. 14, once the data is transmitted to the patient's EMR, the medical device and patient, having been disassociated upon the transmittal of data to the EMR, are no longer displayed on the screen display, and thus a patient and medical device must be identified in order to be associated. FIG. 14 is an exemplary screen display 1400 illustrating the previously identified medical device and patient no longer being displayed on the display once the data has been transferred to the patient's EMR. Area 1410 indicates that a patient is not currently identified, and may be searched for using a search button 1411. Other methods of identifying a patient, as discussed herein, may also be used. Similarly, area 1412 indicates that a medical device is not currently identified, and also may be searched for by the selection of a device search button 1414, although other methods of identifying a medical device may also be used.

Once the data corresponding to the first patient is sent to the first patient's EMR, an identification of a second patient may be received. Upon receiving the identification, the data from the medical device may be acquired, wherein the data corresponds to the second patient, and may be the most updated data corresponding to that patient. The medical device may then be associated with the second patient.

It will be understood that certain features and sub-combinations of utility may be employed without reference to features and sub-combinations and are contemplated within the scope of the claims. Furthermore, the steps performed need not be performed in the order described.

The invention claimed is:
1. A computerized method comprising:
identifying a device based on a device characteristic;
identifying an individual based on an individual characteristic;
linking the device characteristic with the individual characteristic when a command is received to link the device with the individual;

locating the device characteristic in data and using the device characteristic to associate the data with the individual characteristic when the data is obtained from the device subsequent to or concurrent with the command;

loading the data having the device characteristic linked with the individual characteristic to a programming interface, wherein the programming interface consumes at least a portion of the data;

generating a user interface that presents the data loaded to the programming interface, wherein the data loaded to the programming interface is modified to enable editing of the data in the user interface;

transmitting the data loaded to the programming interface to a file having the individual characteristic when an indicator is received via the user interface, wherein the data having the device characteristic is stored in the file having the individual characteristic; and terminating the link between the device characteristic and the individual characteristic in response to transmitting the data to the file having the individual characteristic.

2. The computerized method of claim 1, wherein linking the device characteristic with the individual characteristic when a command is received to link the device with the individual comprises:

prior to terminating the link between the device characteristic and the individual characteristic in response to transmitting the data to the file having the individual characteristic, recognizing that information having the device characteristic corresponds with the individual characteristic based on the link.

3. The computerized method of claim 1, further comprising:

retrieving the data from the device in a raw format, wherein the programming interface retrieves the data via a device messaging services bus that is communicatively coupled to the device; and modifying the data from the raw format to a new format, wherein the new format enables editing of the data in the user interface that presents the data loaded to the programming interface.

4. The computerized method of claim 1, wherein identifying a device based on a device characteristic is responsive to one of a scan of a barcode encoding the device characteristic, a user-input device characteristic, or a result from a search of a database storing device characteristics for a plurality of devices.

5. The computerized method of claim 1, wherein generating the user interface that presents the data loaded to the programming interface comprises:

presenting the individual characteristic, the device characteristic, and at least a portion of the data in the user interface.

6. The computerized method of claim 5, further comprising:

removing one or more of the individual characteristic and the device characteristic from presentation in the user interface in response to terminating the link between the device characteristic and the individual characteristic.

7. The computerized method of claim 1, wherein identifying an individual based on an individual characteristic is responsive to one of a scan of a barcode encoding the individual characteristic, a user-input individual characteristic, or a result from a search of a database storing individual characteristics for a plurality of individuals.

8. The computerized method of claim 1, comprising:

identifying a different individual based on a new individual characteristic subsequent to terminating the link between the device characteristic and the individual characteristic in response to transmitting the data to the file having the individual characteristic;

linking the device characteristic with the new individual characteristic when a command is received to link the device with the new individual;

locating the device characteristic in new data and using the device characteristic to associate the new data with the new individual characteristic;

generating the user interface that presents the new data loaded to the programming interface, wherein the new data loaded to the programming interface is modified to enable editing of the new data in the user interface; and transmitting the new data loaded to the programming interface to another file having the new individual characteristic when an indicator is received via the user interface, wherein the new data that includes the device characteristic is stored in the another file having the individual characteristic.

9. One or more non-transitory computer-readable storage media having computer-executable instructions thereon to perform a method when executed, the method comprising:

for each of a plurality of devices:

identifying a device based on a device characteristic;

identifying an individual based on an individual characteristic;

linking the device characteristic with the individual characteristic when a command is received to link the device with the individual;

locating the device characteristic in data and using the device characteristic to associate the data with the individual characteristic when data is obtained from the device subsequent to or concurrent with the command;

loading the data having the device characteristic linked with the individual characteristic to a programming interface, wherein the programming interface consumes at least a portion of the data;

generating a user interface that presents the data loaded to the programming interface, wherein the data loaded to the programming interface is modified to enable editing of the data in the user interface;

transmitting the data loaded to the programming interface to a file having the individual characteristic when an indicator is received via the user interface, wherein the data having the device characteristic is stored in the file having the individual characteristic; and terminating the link between the device characteristic and the individual characteristic in response to transmitting the data to the file having the individual characteristic.

10. The one or more non-transitory computer-readable media of claim 9, having computer-executable instructions thereon to perform a method when executed, the method comprising:

generating a directory of the plurality of devices; and updating the directory of the plurality of devices to reflect whether, for each of the plurality of devices, a device characteristic is currently linked to an individual characteristic.

11. The one or more non-transitory computer-readable media of claim 9, having computer-executable instructions thereon to perform a method when executed, the method comprising:

managing links between the plurality of devices and one or more individuals.

12. The one or more non-transitory computer-readable media of claim 9, having computer-executable instructions thereon to perform a method when executed, the method comprising:
terminating the link between the device characteristic and the individual characteristic when the device characteristic cannot be located in the data; and
subsequently re-linking the device characteristic with the individual characteristic when the device characteristic is located in subsequently-obtained data and the device characteristic is not currently linked to another individual characteristic.

13. The one or more non-transitory computer-readable media of claim 9, having computer-executable instructions thereon to perform a method when executed, the method comprising:
retrieving the data from the device in a raw format, wherein a programming interface retrieves the data via a device messaging services bus that is communicatively coupled to the device;
modifying the data from the raw format to a new format, wherein the new format enables editing of the data in the user interface that presents the data loaded to the programming interface; and
presenting the individual characteristic, the device characteristic, and at least a portion of the data in the user interface.

14. The one or more non-transitory computer-readable media of claim 13, having computer-executable instructions thereon to perform a method when executed, the method comprising:
removing one or more of the individual characteristic and the device characteristic from presentation in the user interface in response to terminating the link between the device characteristic and the individual characteristic.

15. The one or more non-transitory computer-readable media of claim 9, having computer-executable instructions thereon to perform a method when executed, the method comprising:
modifying the at least a portion of the data presented in the user interface in response to an editing command received via the user interface; and
transmitting the data, as modified, to the file having the individual characteristic when an indicator is received via the user interface, wherein the data, as modified and having the device characteristic, is stored in the file having the individual characteristic.

16. The one or more non-transitory computer-readable media of claim 9, having computer-executable instructions thereon to perform a method when executed, the method comprising:
suggesting the device to a user for linking the device characteristic to the individual characteristic.

17. The one or more non-transitory computer-readable media of claim 16, having computer-executable instructions thereon to perform a method when executed, the method further comprising:
subsequent to identifying the individual based on the individual characteristic, using a diagnosis of the individual to identify the device for suggestion to the user for linking the device characteristic to the individual characteristic.

18. The one or more non-transitory computer-readable media of claim 9, having computer-executable instructions thereon to perform a method when executed, the method comprising:
prior to terminating the link between the device characteristic and the individual characteristic in response to transmitting the data to the file having the individual characteristic:
recognizing that data having the device characteristic corresponds with the individual characteristic based on the link; and
recognizing that information having the individual characteristic corresponds with the device characteristic based on the linking the device characteristic with the individual characteristic.

19. The one or more non-transitory computer-readable media of claim 9, having computer-executable instructions thereon to perform a method when executed, the method comprising:
routing the data having the device characteristic to a database for storage in a flowsheet subsequent to or concurrently with linking the device characteristic with the individual characteristic; and
modifying the data stored in the flowsheet when an editing command is received.

20. A system comprising:
a memory;
a processor coupled to the memory; and
one or more modules to, when executed by the processor:
identify a device based on a device characteristic;
identify an individual based on an individual characteristic:
link the device characteristic with the individual characteristic when a command is received to link the device with the individual;
locate the device characteristic in data and use the device characteristic to associate the data with the individual characteristic when data is obtained from the device subsequent to or concurrent with the command;
load the data having the device characteristic linked with the individual characteristic to a programming interface, wherein the programming interface consumes at least a portion of the data;
generate a user interface that presents the data loaded to the programming interface, wherein the data loaded to the programming interface is modified to enable editing of the data in the user interface;
transmit the data loaded to the programming interface to a file having the individual characteristic when an indicator is received via the user interface, wherein the data that includes the device characteristic is stored in the file having the individual characteristic; and
terminate the link between the device characteristic and the individual characteristic in response to transmission of the data to the file having the individual characteristic.

* * * * *